United States Patent
Biancolillo et al.

(10) Patent No.: US 9,835,574 B2
(45) Date of Patent: Dec. 5, 2017

(54) GAS MEASUREMENT DEVICE AND MEASUREMENT METHOD THEREOF

(71) Applicant: STMicroelectronics S.r.l., Agrate Brianza (IT)

(72) Inventors: Pasquale Biancolillo, Pedara (IT); Angelo Recchia, Fasano (IT); Pasquale Franco, Placanica (IT); Antonio Cicero, Palermo (IT); Giuseppe Bruno, Paterno (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 170 days.

(21) Appl. No.: 14/726,823

(22) Filed: Jun. 1, 2015

(65) Prior Publication Data

US 2016/0003757 A1    Jan. 7, 2016

(30) Foreign Application Priority Data

Jul. 2, 2014   (IT) ............................... MI2014A1197

(51) Int. Cl.
*G01N 27/12* (2006.01)
*G01N 27/18* (2006.01)

(52) U.S. Cl.
CPC .......... *G01N 27/121* (2013.01); *G01N 27/18* (2013.01)

(58) Field of Classification Search
CPC ............................ G01N 27/121; G01N 27/18
See application file for complete search history.

(56) References Cited

U.S. PATENT DOCUMENTS

| 2,701,832 A | * | 2/1955 | Marsden, Jr. ........ G01N 27/121 338/308 |
| 2,949,765 A | * | 8/1960 | Thayer ............... G01N 27/4162 324/443 |
| 3,905,230 A | * | 9/1975 | Calvet ..................... G01D 1/16 73/204.17 |

(Continued)

FOREIGN PATENT DOCUMENTS

| DE | 102008005693 A1 | 7/2008 |
| EP | 0698786 A1 | 2/1996 |
| JP | 2006010670 A | * 1/2006 |

OTHER PUBLICATIONS

Italian Search Report and Written Opinion for IT MI2014A001197 dated Mar. 5, 2015 (9 pages).

*Primary Examiner* — David Bolduc
(74) *Attorney, Agent, or Firm* — Gardere Wynne Sewell LLP

(57) ABSTRACT

A gas measurement device measures gas using a gas sensor including a sense resistance exposed to the gas and a reference resistance not exposed to the gas. The gas measurement device applies a first current value and a second current value to the sensor. A detector functions to detect a first resistance variation and a second resistance variation of the sense resistance exposed to the gas with respect to the reference resistance as a function of the first current value and the second current value, respectively. The resistance variation dependent on relative humidity is then determined as a function of the first and second resistance variations and a first constant. The resistance variation dependent on gas content is then determined as a function of the first and second resistance variations and a second (different) constant.

11 Claims, 3 Drawing Sheets

(56) References Cited

U.S. PATENT DOCUMENTS

| | | | | |
|---|---|---|---|---|
| 4,043,196 A * | 8/1977 | Trageser | G01F 1/6986 | 73/204.14 |
| 4,063,447 A | 12/1977 | Mathison | | |
| 4,210,024 A * | 7/1980 | Ishiwatari | G01D 3/0365 | 374/1 |
| 4,378,691 A * | 4/1983 | Terada | G01N 27/121 | 338/34 |
| 4,456,902 A * | 6/1984 | Komine | G01N 27/121 | 204/412 |
| 4,532,797 A * | 8/1985 | Yang | G01N 27/18 | 324/696 |
| 4,649,736 A * | 3/1987 | Austin | G01N 27/121 | 338/35 |
| 4,888,987 A * | 12/1989 | Zhang | G01D 5/12 | 374/178 |
| 4,896,143 A * | 1/1990 | Dolnick | G01N 27/124 | 340/634 |
| 5,031,126 A | 7/1991 | McCulloch et al. | | |
| 5,117,691 A * | 6/1992 | Fraser | G01N 27/18 | 73/204.15 |
| 5,551,283 A * | 9/1996 | Manaka | G01F 1/6845 | 340/634 |
| 5,789,659 A * | 8/1998 | Williams | G01N 27/12 | 204/411 |
| 2005/0066707 A1* | 3/2005 | Katsuki | G01N 27/18 | 73/23.21 |
| 2005/0155405 A1* | 7/2005 | Sasaki | G01N 27/16 | 73/1.06 |
| 2005/0228596 A1* | 10/2005 | Shoji | G01N 27/18 | 702/24 |
| 2007/0169541 A1 | 7/2007 | Norbeck et al. | | |
| 2009/0133472 A1* | 5/2009 | Tada | G01N 27/18 | 73/31.05 |
| 2011/0257897 A1* | 10/2011 | Watanabe | G01N 27/128 | 702/23 |
| 2012/0247184 A1* | 10/2012 | Kitanoya | G01N 27/18 | 73/25.05 |
| 2013/0256825 A1* | 10/2013 | Humbert | H01L 27/16 | 257/467 |
| 2013/0298638 A1* | 11/2013 | WWatanabe | G01N 27/18 | 73/23.31 |
| 2015/0377813 A1* | 12/2015 | Biancolillo | B81B 7/02 | 257/467 |

* cited by examiner

GAS MEASUREMENT DEVICE AND MEASUREMENT METHOD THEREOF

PRIORITY CLAIM

This application claims priority from Italian Application for Patent No. MI2014A001197 filed Jul. 2, 2014, the disclosure of which is incorporated by reference.

TECHNICAL FIELD

The present disclosure relates to a gas measurement device and measurement method.

BACKGROUND

A thermal conductivity detector (TCD) is well known in the state of the art. This is an environmental sensor device widely used for the measurement of the amount of gas in the environment. The operation is based on the fact that each gas has an inherent thermal conductivity and a filament (thermal resistor) changes its temperature as a function of the amount of gas that surrounds it. The most appropriate sensing element shape is that of a suspended thin finger, for which the temperature of the central part can locally reach even values of several hundred degrees. The feature that the finger is totally suspended allows for enhancing the amount of heat exchange with the gas in which it is immersed. The warming effect of the suspended finger is induced through an electrical stress of the sensor, that is by the flow of the current through the finger. The sensor is able to better discriminate the gases whose conductivity is much different than normal air (roughly nitrogen $N_2$ (79%), oxygen $O_2$ (19%), carbon dioxide $CO_2$ (0.04%), plus other gases with negligible quantities: for example the carbon oxide CO is a few ppm).

When a current flows through the finger, the value of the resistance of the finger changes. The measurement of the resistance value allows for measuring the conductivity of the gas mixture which depends of the molar fraction of the gas of interest.

However, it is difficult in principle to discriminate which gas is mainly responsible for the conductivity variation of the mixture of gas. For example, carbon dioxide $CO_2$ has a lower thermal conductivity than dry air, therefore if its percentage increases inside the mixture, this will raise the temperature of the sensor with a consequent increase of the value of the measured resistance.

The TCD sensor operates in accordance with the thermodynamic equilibrium among heat generated by the current flow, heat exchange with the material of which the sensor is made (e.g. polysilicon crystalline), and heat exchange with the gas mixture surrounding it. The ambient temperature determines the equilibrium value of the sensor in standard dry air. To take into account and compensate the variation of ambient temperature a Wheatstone bridge as the sensor structure could be used. The reference branches of the bridge are of the same nature and positioned in the vicinity of the sensor so as to be sensitive to the same way to changes in ambient temperature, with the difference that these branches will not be exposed to the mixture of gas as is the sensor.

The Relative Humidity (RH) is the amount of water vapor (gas) present in the environment compared to a saturated environment in the same conditions of pressure and temperature. The thermal conductivity of water vapor is much larger than the dry air therefore an increase in relative humidity produces a lowering of the temperature of the sensor with a consequent reduction of the value of the measured resistance. The contribution of the RH value of the measured resistance could be $\frac{1}{10}$ compared to the change of resistance in the presence of carbon dioxide $CO_2$, therefore, this is a parameter to measure and correct. Typically the correction is made by means of a dedicated sensor for the measurement of the RH.

SUMMARY

One aspect of the present disclosure is to provide a gas measurement device of simple architecture.

One aspect of the present disclosure is a gas measurement device for measuring gas by means of a gas sensor comprising at least one resistance exposed to at least one gas and at least one reference resistance not exposed to the gas, said gas measurement device comprising: a control device configured to manage the gas sensor so that the gas sensor receives at least a first current value and a second current value, a detector to detecting a first resistance variation and a second resistance variation of the resistance exposed to the gas with respect to the reference resistance as a function of the first current value and the second current value respectively, and a calculation circuit configured to calculate at least a first and a second equations wherein the first equation is given by the difference between the first resistance variation multiplied by a first constant and the second resistance variation while the second equation is given by the difference between the first resistance variation multiplied by a second constant and the second resistance variation, the first constant and the second constant having different values.

BRIEF DESCRIPTION OF THE DRAWINGS

For a better understanding of the present disclosure, a preferred embodiment thereof is now described, purely by way of non-limiting example and with reference to the annexed drawings, wherein.

DETAILED DESCRIPTION

Figure 1:
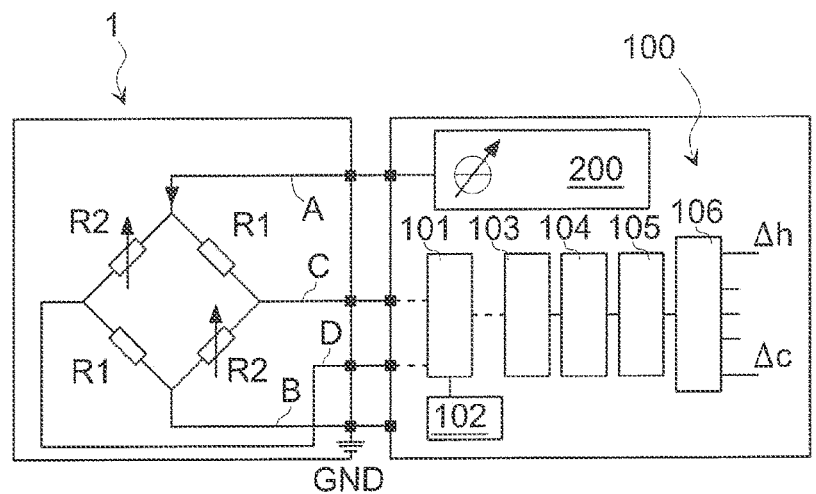
FIG. 1 shows a block diagram of a measurement apparatus comprising a gas sensor device and a gas measurement device according to the present disclosure.

FIG. 1 shows a block diagram of a measurement apparatus comprising a gas sensor device 1, that is a TCD sensor, and a gas measurement device 100 according to the present disclosure.

The gas sensor device 1 comprises at least one variable resistance R2 exposed to the gas and a reference resistance R1 which is not exposed to the gas; the reference resistor R1 has the value of the resistance R2 at the condition of dry air and room temperature. The value of the resistance R2 varies when exposed to the gas, the humidity and the temperature. Preferably, the gas sensor device 1 is a Wheatstone bridge including a couple of reference resistors R1 and a couple of resistors R2 exposed to the gas; the use of a Wheatstone bridge allows for minimizing the dependence on the ambient temperature. The four connecting nodes A-D of the terminals of the resistances R1 and R2 of the Wheatstone bridge 1 are connectible respectively with a variable current generator 200, to ground GND and to the gas measurement device 100 able to receive the voltage signal at the output of the Wheatstone bridge 1.

The measurement device 100 (FIG. 1) comprises preferably a temperature sensor 102 in the case wherein it is necessary to provide a temperature compensation of the signals at the output of the sensor device 1. The measurement device 100 comprises preferably a multiplexer 101, configured to receive the output signal of the sensor device 1 or the output signal of the temperature sensor 102. The measurement device 100 comprises a device 103 configured to amplify the signal at the output of the multiplexer, an analog-to-digital converter 104 for converting the analog signals at the input into a digital signal at the output, a digital controller 105 for processing the signal deriving from the sensor device and an interface 106 for outputting the processed signal to the outside.

Figure 2:
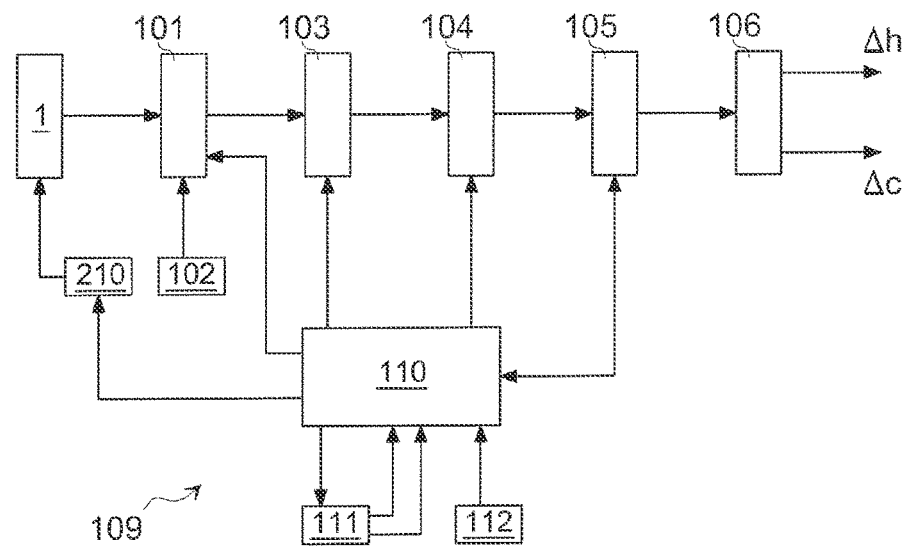
FIG. 2 shows a more detailed block diagram of the gas measurement device according to the present disclosure.

The measurement device 100 is shown in more detail in FIG. 2. The device 103 is preferably a low noise analog front end comprising the cascade of two fully differential switched-capacitor amplifiers configured to amplify the signal at the output of the multiplexer 101 and to compensate the offset of the gas sensor 1 or the temperature sensor 102. The low noise analog front end 103 makes use of both chopping and correlated double sampling techniques, which ensure offset canceling and low frequency noise filtering.

A managing device 109 manages the devices 101-106 and the variable current generator 210; the managing device 109 manages the timing of the low noise analog front end 103, the analog-to-digital converter 104 and the digital controller 105. The managing device comprises a clock generator 111 configured to send two different clock signals at different frequency, for example 1 Mhz and 40 Khz, to a phase generator 110 which receives the output of the bit register 112.

When a gas having a concentration m is inside the gas sensor 1 at a relative humidity n, the managing device 109 is configured to effectuate the following steps:

managing the variable current generator 210 to send a first current value Il to the gas sensor 1 and detect the resistance variation $\Delta R(Il)$ of the resistances R2 with respect to the reference resistances R1;

managing the variable current generator 210 to send a second current value Ih to the gas sensor 1 and detect the resistance variation $\Delta R(Ih)$ of the resistances R2 with respect to the reference resistances R1;

managing the digital controller 105 to calculate the resistance variation $\Delta h$ depending only on the relative humidity variation by means of the following equation $\Delta h = K1 \times \Delta R(Il) - \Delta R(Ih)$ and the resistance variation $\Delta c$ depending only on the gas concentration variation by means of the following equation $\Delta c = K2 \times \Delta R(Il) - \Delta R(Ih)$ wherein K1 and K2 are constants having different values. In this way the calculation of the above equations allow obtaining the indirect measure of the relative humidity alone, independently from the gas concentration, and of the gas concentration alone, independently from the relative humidity, and managing the interface 106 to output the resistance variations $\Delta h$ and $\Delta c$.

In the case wherein the concentrations of a first and a second gases need to be measured, the digital controller 105 is configured to:

manage the variable current generator 210 to send a first current value Il to the gas sensor 1 and detect the resistance variation $\Delta R(Il)$ of the resistances R2 with respect to the reference resistances R1;

manage the variable current generator 210 to send a second current value Ih to the gas sensor 1 and detect the resistance variation $\Delta R(Ih)$ of the resistances R2 with respect to the reference resistances R1;

manage the digital controller 105 to calculate the resistance variation $\Delta c1$ depending only on the concentration variation of the first gas by means of the following equation $\Delta c1 = K21 \times \Delta R(Il) - \Delta R(Ih)$ and the resistance variation $\Delta c2$ depending only on the concentration variation of the second gas by means of the following equation $\Delta c2 = K22 \times \Delta R(Il) - \Delta R(Ih)$, wherein K21 and K21 are constants having different values. In this way the calculation of the above equations allow obtaining the indirect measure of the concentration of the first gas independently from the concentration of the second gas and vice versa, and manage the interface 106 to output the resistance variations $\Delta c1$ and $\Delta c2$.

Figure 3:
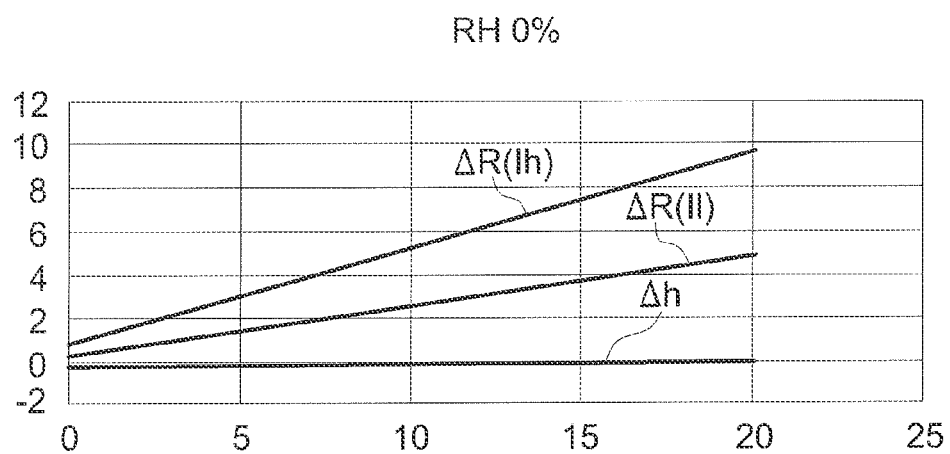
FIGS. 3-5 show the waveforms of the resistance variations $\Delta R(Il)$, $\Delta R(Ih)$ as a function of the concentration of carbon dioxide $CO_2$ and the waveform of a resistance value as a function of the relative humidity RH.
Figure 4:
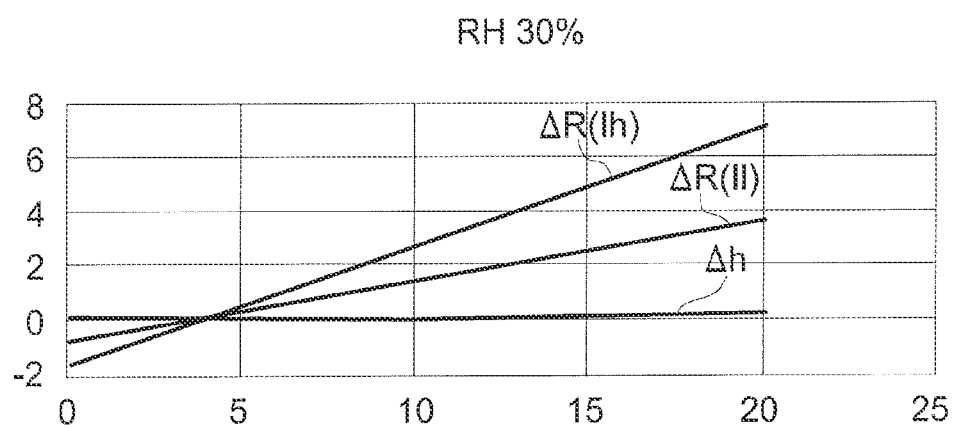
Figure 5:
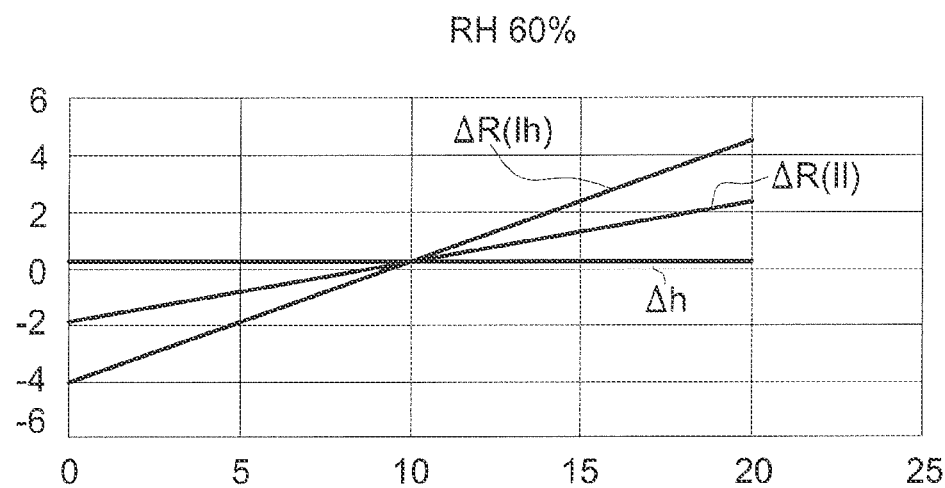

In FIGS. 3-5 the waveforms of the resistance variations $\Delta R(Il)$, $\Delta R(Ih)$ are shown wherein on the X axis the variation of the concentration of the gas is indicated while on the Y-axis the variation of the sensor resistance is indicated at the condition for a relative humidity RH=0, RH=30% and RH=60%. The further waveform is the resistance value $\Delta h = K1 \times \Delta R(Il) - \Delta R(Ih)$ which is independent on the variation of the concentration of the gas and depends only on the relative humidity RH.

Figure 6:
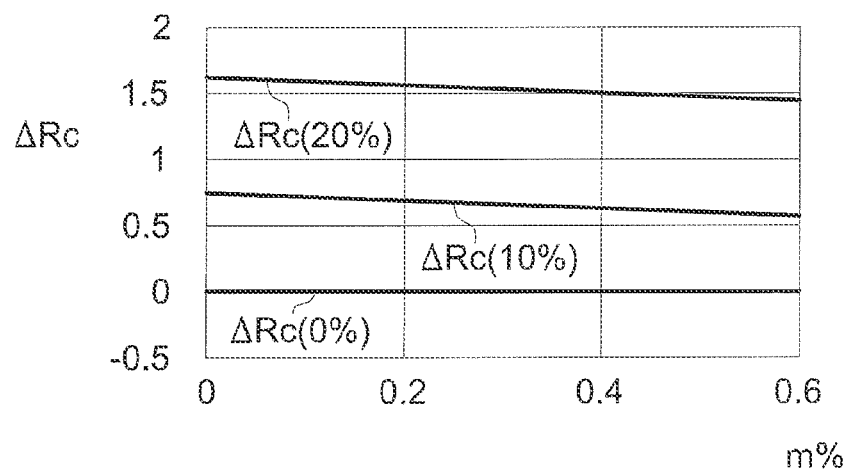
FIG. 6 shows the waveforms of the resistance variation value as a function of the different concentrations of $CO_2$.

FIG. 6 show the resistance values $\Delta c = K2 \times \Delta R(Il) - \Delta R(Ih)$ for gas concentrations m=0%, m=10% and m=20% which depend only on the concentration variation of the carbon dioxide $CO_2$ and are independent on the relative humidity RH.

Preferably the constants K1 and K2 have respectively the values of 1.827 and 2.165. A method for calculating the appropriate value of the constants K1 and K2 is now described.

The thermal conductivity of a gas mixture depends on the molar fraction of the gases of the mixture, on the conductivity of the gases and on the dynamic viscosity according to the Chapman-Enskog model.

In first approximation, starting from the Chapman-Enskog model ("The mathematical theory of non-uniform gases: an account of kinetic theory of viscosity, thermal conduction and diffusion in gases" S. Chapman, T G. Cowling 1970, incorporated by reference) and obtaining a linear equation, the thermal conductivity of a gas mixture is linearly proportional to the temperature and the concentration of gases of the mixture.

The resistance variation $\Delta R$ (that is the variation of the resistance R2 with respect to the reference resistance R1) is a linear function of both the concentration of the matters to be examined (the concentration of gas and the humidity or the concentrations of two gases) and the current flowing through the resistance R2, preferably, in the case wherein the sensor is a Wheatstone bridge, the resistance variation $\Delta R$ is a linear function of both the concentration of the matters to be examined and the current flowing through the bridge 1.

In fact, balancing and solving the equation for the thermoelectric equilibrium of the system comprising the bridge 1 and the gas mixture, the resulting temperature at the equilibrium is approximately a linear function of the concentrations of gas and humidity and of the current flowing through the bridge 1.

At the thermoelectric equilibrium it is necessary to consider the power dissipated by Joule effect on the resistance R2, $P=R\times I^2$ wherein I is the current flowing through the bridge 1, and the amount of the heat exchange due to the thermal conductivity of the gas mixture, $$\frac{Q}{T} = K \times \frac{A}{dx} \Delta T$$

where A is the surface of the resistance R2, dx is the thickness of the resistance R2 and $\Delta T$ is the temperature variation; at the thermoelectric equilibrium it is obtained that the temperature variation $\Delta T$ is a linear function of the concentrations of gas and humidity and of the current flowing through the bridge 1

The resistance variation $\Delta R$ depends on the temperature variation $\Delta T$ according to the $\Delta R=R0\times(1+\alpha\Delta T)$ where a is the thermal coefficient of the resistance and depends on the material of the resistive bridge and R0 is the resistance value at room temperature, therefore even the resistance variation $\Delta R$, so as the temperature variation $\Delta T$, is a linear function of the concentrations of gas and humidity and of the current flowing through the bridge 1. The resistance variation $\Delta R$ as linear function of the concentrations of gas and humidity and of the current flowing through the bridge 1 can be represented by the following equation $\Delta R=(a\times I+b)\times m+(c\times I+d)\times n$ wherein m is the concentration of gas, n is the concentration of humidity, I is the current flowing through the bridge 1 and a, b, c and d are parameters depending on the balance of the system which are determined by effectuating four calibration measurements with known gas and humidity concentrations and currents.

After determining the parameters a, b, c and d two measurements of the unknown mixture are effectuated with the unknown concentrations m and n and two different current values Il and Ih; solving said two equations and calculating the resistance variation as function of the current, that is $\Delta R(Il)$ and $\Delta R(Ih)$, the unknown values of the concentrations m and n are obtained.

Considering the generic equation $\Delta R=K\times\Delta R(Il)-\Delta R(Ih)$, exist only two values K1 and K2 of K which allow the m and n concentration components to become null. The equation becomes: $\Delta R(K)=(a\times(K\times Il-Ih)+b\times(K-1))\times m+(c\times(K\times Il-Ih)+d\times(K-1))\times n$ and setting equal to zero the m and n concentration components the values $$K1 = \frac{a\times Ih+b}{a\times Il+b} \text{ and } K2 = \frac{c\times Ih+d}{c\times Il+d}$$

are obtained. In this way each one of the results $\Delta c(K2)$ and $\Delta h(K1)$ depends on the concentration variations only of one of two unknown concentrations.

The invention claimed is:

1. A gas measurement device for measuring gas using a gas sensor comprising a sensing resistance exposed to a gas and at least one reference resistance not exposed to the gas, said gas measurement device comprising:
 a managing device configured to manage the gas sensor so that the gas sensor receives at least a first current value Il and a second current value Ih,
 a detector configured to detect a first resistance variation $\Delta R(Il)$ of said sensing resistance exposed to the gas with respect to the reference resistance as a function of the first current value Ih and detect a second resistance variation $\Delta R(Ih)$ of the same sensing resistance exposed to the gas with respect to the same reference resistance as a function of the second current value Ih, and
 a calculation circuit configured to calculate: a resistance variation dependent on relative humidity and a resistance variation dependent on gas concentration as a function of first resistance variation $\Delta R(Il)$ and the second resistance variation $\Delta R(Ih)$.

2. The gas measurement device according to claim 1, wherein the calculation circuit is configured to:
 calculate the resistance variation dependent on relative humidity as a function of a difference between the first $\Delta R(Il)$ resistance variation multiplied by a first constant K1 and the second $\Delta R(Ih)$ resistance variation; and
 calculate the resistance variation dependent on gas concentration as a function of a difference between the first $\Delta R(Il)$ resistance variation multiplied by a second constant K2 and the second resistance variation $\Delta R(Ih)$,
 wherein the first constant and the second constant have different values.

3. The gas measurement device according to claim 1, wherein the calculation of the resistance variation dependent relative humidity utilizes the following equation $K1\times\Delta R(Il)-\Delta R(Ih)$ and the calculation of the resistance variation dependent on gas concentration utilizes the following equation $K2\times\Delta R(Il)-\Delta R(Ih)$, wherein K1 and K2 are first and second, different, constants.

4. The gas measurement device according to claim 3, wherein the values of the first and second constants are 1.827 and 2.165.

5. A measurement apparatus, comprising:
 a gas sensor comprising a sensing resistance exposed to a gas and a reference resistance not exposed to the gas; and
 a gas measurement device comprising:
  a managing device configured to manage the gas sensor so that the gas sensor receives at least a first current value Il and a second current value Ih,
  a detector configured to measure a first resistance variation $\Delta R(Il)$ of said sensing resistance exposed to the gas with respect to the reference resistance as a function of the first current value Ih and measure a second resistance variation $\Delta R(Ih)$ of the same sensing resistance exposed to the gas with respect to the same reference resistance as a function of the second current value Ih,
  a calculation circuit configured to calculate: a resistance variation dependent on relative humidity and a resistance variation dependent on gas concentration as a function of first resistance variation $\Delta R(Il)$ and the second resistance variation $\Delta R(Ih)$.

6. The measurement apparatus according to claim 5, wherein the calculation circuit is configured to:
 calculate the resistance variation dependent on relative humidity as a function of a difference between the first $\Delta R(Il)$ resistance variation multiplied by a first constant K1 and the second $\Delta R(Ih)$ resistance variation; and
 calculate the resistance variation dependent on gas concentration as a function of a difference between the first $\Delta R(Il)$ resistance variation multiplied by a second constant K2 and the second resistance variation $\Delta R(Ih)$,
 wherein the first constant and the second constant have different values.

7. The measurement apparatus according to claim 6, wherein said gas sensor is a Wheatstone bridge including said sensing resistance and said reference resistance.

8. A method for measuring gas by means of a gas sensor comprising a sensing resistance exposed to a gas and a reference resistance not exposed to the gas, said method comprising:
sending a first current value Il to the gas sensor,
detecting a first resistance variation $\Delta R(Il)$ of the sensing resistance exposed to the gas with respect to the reference resistance in response to said first current value Il,
sending a second current value Ih to the gas sensor,
detecting a second resistance variation $\Delta R(Ih)$ of the same sensing resistance exposed to the gas with respect to the same reference resistance in response to said second current value Ih, and
calculating a resistance variation dependent on relative humidity and calculating a resistance variation dependent on gas concentration as a function of the first resistance variation $\Delta R(Il)$ and the second resistance variation $\Delta R(Ih)$.

9. The method according to claim 8, wherein:
calculating the resistance variation dependent on relative humidity comprises calculating a difference between the first $\Delta R(Il)$ resistance variation multiplied by a first constant K1 and the second $\Delta R(Ih)$ resistance variation; and
calculating the resistance variation dependent on gas concentration comprises calculating a difference between the first $\Delta R(Il)$ resistance variation multiplied by a second constant K2 and the second resistance variation $\Delta R(Ih)$,
wherein the first constant and the second constant have different values.

10. The method according to claim 9, wherein the calculation of the resistance variation dependent relative humidity utilizes the following equation $K1 \times \Delta R(Il) - \Delta R(Ih)$ and the calculation of the resistance variation dependent on gas concentration utilizes the following equation $K2 \times \Delta R(Il) - \Delta R(Ih)$, wherein K1 and K2 are first and second, different, constants.

11. The method according to claim 10, wherein the values of the first and second constants are 1.827 and 2.165.

* * * * *

UNITED STATES PATENT AND TRADEMARK OFFICE
CERTIFICATE OF CORRECTION

PATENT NO. : 9,835,574 B2  
APPLICATION NO. : 14/726823  
DATED : December 5, 2017  
INVENTOR(S) : Pasquale Biancolillo et al.

It is certified that error appears in the above-identified patent and that said Letters Patent is hereby corrected as shown below:

In the Specification

At Column 5, Line number 16, please replace the phrase [[where a is]] with the phrase -- where $\alpha$ is --.

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*